US011337901B2

(12) United States Patent
Taima

(10) Patent No.: US 11,337,901 B2
(45) Date of Patent: May 24, 2022

(54) WATER-IN-OIL EMULSION COMPOSITION

(71) Applicant: KAO CORPORATION, Tokyo (JP)

(72) Inventor: Hidetoshi Taima, Machida (JP)

(73) Assignee: KAO CORPORATION, Tokyo (JP)

( * ) Notice: Subject to any disclaimer, the term of this patent is extended or adjusted under 35 U.S.C. 154(b) by 172 days.

(21) Appl. No.: 16/617,837

(22) PCT Filed: May 30, 2018

(86) PCT No.: PCT/JP2018/020796
§ 371 (c)(1),
(2) Date: Nov. 27, 2019

(87) PCT Pub. No.: WO2018/221602
PCT Pub. Date: Dec. 6, 2018

(65) Prior Publication Data
US 2020/0246231 A1 Aug. 6, 2020

(30) Foreign Application Priority Data
May 30, 2017 (JP) .............................. JP2017-107247

(51) Int. Cl.
| A61K 8/00 | (2006.01) |
| A61K 8/06 | (2006.01) |
| A61K 8/37 | (2006.01) |
| A61K 8/68 | (2006.01) |
| A61K 8/86 | (2006.01) |
| A61K 8/891 | (2006.01) |
| A61K 8/92 | (2006.01) |

(52) U.S. Cl.
CPC .............. *A61K 8/064* (2013.01); *A61K 8/37* (2013.01); *A61K 8/68* (2013.01); *A61K 8/86* (2013.01); *A61K 8/891* (2013.01); *A61K 8/92* (2013.01)

(58) Field of Classification Search
CPC . A61K 8/064; A61K 8/31; A61K 8/37; A61K 8/86; A61K 8/92; A61K 8/891; A61K 8/68
USPC ....................................................... 424/70.1
See application file for complete search history.

(56) References Cited

U.S. PATENT DOCUMENTS

| 5,036,108 A * | 7/1991 | Asahi ..................... A61K 8/894 514/772 |
| 5,415,855 A * | 5/1995 | Critchley ................. A61Q 5/00 424/61 |
| 6,447,790 B1 | 9/2002 | Ishii et al. |
| 2003/0158363 A1* | 8/2003 | Nakanishi ............... A61Q 19/00 528/25 |
| 2004/0219178 A1* | 11/2004 | Fukuda ..................... A61K 8/37 424/401 |
| 2004/0223936 A1* | 11/2004 | Fecht ...................... A61Q 19/00 424/70.12 |
| 2010/0055220 A1 | 3/2010 | Akatsuka et al. |
| 2012/0301523 A1 | 11/2012 | Fukui et al. |
| 2013/0005808 A1 | 1/2013 | Kachi et al. |
| 2014/0363475 A1* | 12/2014 | Tanishima .............. A61K 8/922 424/401 |
| 2015/0030647 A1* | 1/2015 | Suzuki ................. A61K 8/0241 424/401 |
| 2015/0037418 A1* | 2/2015 | Suzuki ................... A61K 8/898 424/489 |
| 2015/0202137 A1 | 7/2015 | Kitajima et al. |

FOREIGN PATENT DOCUMENTS

| EP | 2 263 639 A2 | 12/2010 |
| EP | 2 505 182 A1 | 10/2012 |
| JP | 2000-355531 A | 12/2000 |
| JP | 2001-187711 A | 7/2001 |
| JP | 2002-193741 A | 7/2002 |
| JP | 2002-363029 A | 12/2002 |
| JP | 2003-226609 A | 8/2003 |
| JP | 2010-513221 A | 4/2010 |
| JP | 2010-184912 A | 8/2010 |
| JP | 2011-21007 A | 2/2011 |
| JP | 2011-111401 A | 6/2011 |
| JP | WO 2011/118497 A1 | 9/2011 |
| JP | 2013107865 A * | 11/2011 ............... A61K 8/97 |

(Continued)

OTHER PUBLICATIONS

Extended European Searct Report dated Mar. 3, 2021 in European Patent Application No. 18809288.6, citing document AO therein, 11 pages.
International Search Report dated Sep. 4, 2018 in PCT/JP2018/020796 filed on May 30, 2018,citing documents AB-AE and AJ-AU therein, 2 pages.
Sekine, S., et al., Nikko Chemicals Co., Ltd., "1. Emulsification", Personal Care Handbook, published Jun. 7, 2016 by Chuo Printing Co., Ltd., pp. 604-606 (with unedited computer generated English translation).

(Continued)

*Primary Examiner* — Eisa B Elhilo
(74) *Attorney, Agent, or Firm* — Oblon, McClelland, Maier & Neustadt, L.L.P.

(57) ABSTRACT

The present invention provides a water-in-oil emulsion composition having a high water occlusive of a coating film and having good skin protective feeling and glossiness.
The water-in-oil emulsion composition is provided containing the following components (A), (B), (C), (D) and (E): (A) 1% by mass or more and 15% by mass or less of a lipophilic surfactant having an HLB of 2-6; (B) 0.15% by mass or more and 8% by mass or less of a dextrin fatty acid ester having 8-22 carbon atoms in the fatty acid moiety; (C) 1% by mass or more and 20% by mass or less of one or more oily components selected from a dimer acid ester, a fatty acid cholesterol ester having 16-22 carbon atoms, a fatty acid phytosterol ester having 16-22 carbon atoms, and an N-acyl amino acid ester; (D) a hydrocarbon oil that is liquid at 25° C.; and (E) water.

15 Claims, No Drawings

(56) References Cited

FOREIGN PATENT DOCUMENTS

| | | |
|---|---|---|
| JP | 2012-188394 A | 10/2012 |
| JP | 2012-250922 A | 12/2012 |
| JP | 2013-14544 A | 1/2013 |
| JP | 2013-63967 A | 4/2013 |
| JP | 2013-103885 A | 5/2013 |
| JP | 2013-107865 A | 6/2013 |
| JP | 5247127 B2 | 7/2013 |
| JP | 2014-15425 A | 1/2014 |
| JP | 2014-47158 A | 3/2014 |
| JP | 5667383 B2 | 2/2015 |
| JP | 5944707 B2 | 7/2016 |
| JP | 6325293 B2 | 5/2018 |
| JP | 2019-85390 A | 6/2019 |

OTHER PUBLICATIONS

Ohashi, Y., "Development of new vegetable oil-based base with lanolin-like properties and application to cosmetics", Fragrance Journal, Nov. 2013, pp. 55-60 (with unedited computer generated English translation).

Kao Corporation, Moisture Cream(ID#;4406243), Mintel GNPD [online], Nov. 2016, [Retrieved on Jan. 31, 2022], 10 pages, Internet <URL:https://www.gnpd.com>(with machine translation).

\* cited by examiner

WATER-IN-OIL EMULSION COMPOSITION

FIELD OF THE INVENTION

The present invention relates to a water-in-oil emulsion composition.

BACKGROUND OF THE INVENTION

In recent years, paste-like oily components such as dimer acid esters and N-acyl amino acid esters have been known to have excellent water-holding properties, and are used in cosmetics having water-holding capacities (Patent Documents 1 and 2).

(Patent Document 1) JP-A-2010-513221
(Patent Document 2) JP-A-2013-63967

SUMMARY OF THE INVENTION

The present invention provides a water-in-oil emulsion composition comprising the following components (A), (B), (C), (D) and (E):

(A) 1% by mass or more and 15% by mass or less of a lipophilic surfactant having an HLB of from 2 to 6;
(B) 0.15% by mass or more and 8% by mass or less of a dextrin fatty acid ester having 8 to 22 carbon atoms in the fatty acid moiety;
(C) 1% by mass or more and 20% by mass or less of one or more oily components selected from the group consisting of a dimer acid ester, a fatty acid cholesterol ester having 16 to 22 carbon atoms, a fatty acid phytosterol ester having 16 to 22 carbon atoms and an N-acyl amino acid ester,
(D) a hydrocarbon oil that is liquid at 25° C., and
(E) water.

DETAILED DESCRIPTION OF THE INVENTION

The water-in-oil emulsion composition containing therein an oily component having a water-holding capacity such as a dimer acid ester or an N-acyl amino acid ester simply is not yet sufficiently satisfactory in water occlusive, and furthermore, a cosmetic having excellent feeling upon use, feeling after application, and the like is desired.

Accordingly, present invention provides a water-in-oil emulsion composition which is excellent in water occlusive and also excellent in feeling upon use, feeling after application, and the like.

Therefore, the present inventor has produced a water-in-oil emulsion composition containing the oily component having a water-holding capacity such as dimer acid ester or N-acyl amino acid ester, has investigated the characteristics thereof, and has found that when a lipophilic surfactant having a specific HLB value, a dextrin fatty acid ester, and a hydrocarbon oil that is liquid at 25° C. are blended into the water-in-oil emulsion composition at a specific ratio, a water-in-oil emulsion composition which is remarkably improved in water occlusive, is excellent in skin protective feeling and glossiness, and furthermore has excellent storage stability and good feeling after application can be obtained, to complete the present invention.

The water-in-oil emulsion composition of the present invention has excellent water occlusive when applied, that is, a barrier function, is excellent in skin protective feeling and glossiness, has good feeling upon use without stickiness or uncomfortable feeling of the applied skin, and is excellent in stability without separation of the emulsion even when stored for a long period of time.

In the water-in-oil emulsion composition of the present invention, a lipophilic surfactant having an HLB in the range of 2 to 6 as component (A) is used in order to emulsify an oily component and to improve long-term storage stability.

As the lipophilic surfactant having an HLB of from 2 to 6, a nonionic surfactant having an HLB of from 2 to 6 is preferable, and examples thereof include glycerol fatty acid ester, polyglycerol fatty acid ester, propylene glycol fatty acid ester, sorbitan fatty acid ester, polyoxyethylene castor oil, polyoxyethylene hydrogenated castor oil, polyoxyethylene hydrogenated castor oil fatty acid ester, polyethylene glycol fatty acid ester, alkyl glyceryl ether, alkyl polyglyceryl ether, polyoxyethylene alkyl ether, polyoxyethylene alkyl ether fatty acid ester, polyoxyethylene alkyl amine, silicone surfactant, and the like. Examples of the silicone surfactant include polyether modified silicone, polyether/alkyl co-modified silicone, polyglycerol modified silicone, polyglycerol/alkyl co-modified silicone, alkyl/polyether modified silicone, alkyl silicone dendron polyether modified silicone, and the like, each of which includes a linear type, a branched chain type, and cross-linked type of the silicone chain. These are available from Shin-Etsu Chemical Co., Ltd, Dow Corning Toray Co., Ltd., Momentive Performance Materials Japan Inc., Wacker Asahikasei Silicone Co., Ltd., and the like.

Among these, component (A) are preferably the silicone surfactant, polyoxyethylene hydrogeneted castor oil, alkyl glyceryl ether, polyglycerol fatty acid ester, and sorbitan fatty acid ester; more preferably the silicone surfactant, polyoxyethylene hydrogenated castor oil, alkyl glyceryl ether, and polyglycerol fatty acid ester; even more preferably alkyl glyceryl glyceryl ether, polyglycerol fatty acid ester and the silicone surfactant; even more preferably polyglycerol fatty acid ester and the silicone surfactant; and even more preferably the silicone surfactant from the viewpoint of improving emulsifying property, long-term storage stability, and water occlusive and adjusting the viscosity to an appropriate one and viewpoint of achieving good feeling upon use without stickiness or uncomfortable feeling when applying to the skin.

The polyglycerol fatty acid ester preferably has the polyglycerol moiety of a condensate of 2 to 20 glycerins and the fatty acid moiety of a $C_8$-$C_{24}$ fatty acid from the viewpoint of achieving water occlusive, protective feeling of the skin, glossiness, storage stability, and good feeling upon use without stickiness or uncomfortable feeling when applying to the skin. Among these polyglycerol fatty acid esters, a polyglycerol difatty acid ester and a polyglycerol trifatty acid ester are preferable and a polyglycerol difatty acid esters are more preferable from the viewpoints of achieving water occlusive, skin protective feeling, glossiness, storage stability, good feeling upon use without stickiness or uncomfortable feeling when applying to the skin. The fatty acid moiety is preferably a $C_{14}$-$C_{22}$ fatty acid, more preferably a $C_{16}$-$C_{22}$ fatty acid, even more preferably oleic acid, isostearic acid, stearic acid, hydroxy stearic acid, and behenic acid, and even more preferably isostearic acid and stearic acid, and even more preferably isostearic acid.

More specifically, a polyglycerol di $C_{16}$-$C_{22}$ fatty acid ester and a polyglycerol tri $C_{16}$-$C_{22}$ fatty acid ester are preferable; a polyglycerol diisostearate and a polyglycerol triisostearate are more preferable, and a polyglycerol diisostearate is even more preferable.

The polyglycerol moiety of these polyglycerol fatty acid esters is preferably a condensate of 2 to 12 glycerins, more preferably a condensate of 2 to 10 glycerins, even more preferably a condensate of 2 to glycerins, and even more preferably condensate of 2 glycerins, from the viewpoint of water occlusive, skin protective feeling, glossiness and storage stability, good feeling upon use without stickiness or uncomfortable feeling when applying to the skin.

The silicone surfactant is preferably polyether modified silicone, polyglycerol modified silicone, polyether/alkyl co-modified silicone, and polyglycerol/alkyl co-modified silicone, and particularly preferably polyether modified silicone. The silicone chain is preferably a linear type, a branched chain type, and a crosslink type, more preferably a linear type and a branched chain type, and even more preferably a linear type. More specifically, polyether modified silicone having a linear silicone chain, a polyether modified silicone having a branched silicone chain, a polyether/alkyl co-modified silicone having a linear silicone chain, and a polyether/alkyl co-modified silicone having a branched silicone chain are preferable; polyether modified silicone having a linear silicone chain, and a polyether modified silicone having a branched silicone chain are more preferable; a polyether modified silicone having a linear silicone chain is even more preferable.

From the viewpoint of particularly improving emulsifying property, long-term storage stability and water occlusive, and from the viewpoint of achieving good feeling upon use without stickiness or uncomfortable feeling when applying to the skin, component (A) is preferably polyoxyethylene hydrogenated castor oil, alkyl glyceryl ether, polyglycerol fatty acid ester, polyether modified silicone having a linear silicone chain, and polyether modified silicone having a branched silicone chain; more preferably alkyl glyceryl ether, polyglycerol fatty acid ester, and polyether modified silicone having a linear silicone chain; even more a polyglycerol fatty acid ester and a polyether modified silicone having a linear silicone chain; and particular preferably polyether modified silicone having a linear silicone chain.

One or two or more of these can be used, and it is preferable to use two or more of them from the viewpoint of improving emulsifying property and long-term storage stability, maintaining excellent water occlusive, being excellent in skin protection feeling, coverage of the skin, and glossiness, and achieving good feeling upon use without stickiness or uncomfortable feeling.

Commercially available products thereof include polyether modified silicone such as silicone BY11-030 (PEG/PPG-19/19 Dimethicone (Dow Corning Toray Co., Ltd), silicone BY22-008M (PEG/PPG-19/19 Dimethicone (Dow Corning Toray Co., Ltd), silicone SH3775M (PEG-12 Dimethicone (Dow Corning Toray Co., Ltd), silicone KF-6015 (PEG-3 dimethicone (Shin-Etsu Chemical Co., Ltd), silicone KF-6017 (PEG-10 dimethicone (Shin-Etsu Chemical Co., Ltd), silicone KF-6028 (PEG-9 polydimethylsiloxyethyl dimethicone (Shin-Etsu Chemical Co., Ltd), etc.; polyoxyethylene hydrogenated castor oil such as EMALEX HC-5 (PEG-5 hydrogenated castor oil (Nihon Emulsion Co., Ltd.), and EMALEX RWIS-315 (PEG-15 hydrogenated castor oil triisostearate) (Nihon Emulsion Co., Ltd.); and isosstearyl glyceryl ether. Among these, silicone BY11-030 (PEG/PPG-19/19 Dimethicone), silicone SH3775M (PEG-12 Dimethicone), silicone KF-6015 (PEG-3 dimethicone), silicone KF-6017 (PEG-10 dimethicone), silicone KF-6028 (PEG-9 polydimethylsiloxyethyl dimethicone), EMALEX HC-5 (PEG-5 hydrogenated castor oil), and isostearyl glyceryl ether are more preferable; and silicone KF-6015 (PEG-3 dimethicone), silicone KF-6017 (PEG-10 dimethicone), and isostearyl glyceryl ether are even more preferable. One or more of them may be used.

HLB (Hydrophilic-Lipophilic Balance <Hydrophilic-Lypophilic Balance>) herein indicates the molecular weight of the hydrophilic group moiety in the total molecular weight of the surfactant, and HLB is obtained by the equation of Griffin.

Component (A) is contained in the water-in-oil emulsion composition of the present invention in an amount of 1% by mass or more and 15% by mass or less. When the content of component (A) is within this range, the emulsifying property, long-term storage stability, and water occlusive of the water-in-oil emulsion composition of the present invention are improved, the viscosity is adjusted to a suitable level, and a good feeling upon use is provided to the applied skin without stickiness and uncomfortable feeling. The content of component (A) is preferably 1.5% by mass or more, more preferably 2% by mass or more, and even more preferably 2.5% by mass or more; and preferably 12% by mass or less, more preferably 10% by mass or less, even more preferably 8% by mass or less, even more preferably 6% by mass or less, even more preferably 5% by mass or less, and even more preferably 4.5% by mass or less from the same viewpoint. The specific range is preferably 1.5% by mass or more and 12% by mass or less, more preferably 2% by mass or more and 10% by mass or less, even more preferably 2% by mass or more and 8% by mass or less, even more preferably 2% by mass or more and 6% by mass or less, even more preferably 2.5% by mass or more and 5% by mass or less, and even more preferably 2.5% by mass or more and 4.5% by mass or less.

In the water-in-oil emulsion composition of the present invention, use of polyglycerol fatty acid ester and a lipophilic surfactant having an HLB of from 2 to 6 other than the polyglycerol fatty acid ester in combination can provide good skin protective feeling and glossiness as well as good long-term storage stability while maintain excellent water occlusive.

When a polyglycerol fatty acid ester and a lipophilic surfactant having an HLB of from 2 to 6 other than the polyglycerol fatty acid ester are used in combination, the content of the polyglycerol fatty acid ester is preferably 0.5% by mass or more and 8% by mass Or less in the water-in-oil emulsion composition of the present invention; and when the content falls within this range, sufficient water occlusive is obtained, skin protective feeling and glossiness is good, feeling of upon use of the applied skin is good without stickiness and uncomfortable feeling, and long-term storage stability is excellent. From the same viewpoints, the content of the polyglycerol fatty acid ester is more preferably 0.7% by mass or more, even more preferably 0.8% by mass or more, and even more preferably 1% by mass or more; and more preferably 7% by mass or less, even more preferably 6% by mass or less, even more preferably 5% by mass or less, and even more preferably by mass or less. The specific range is more preferably 0.7% by mass or more and 7% by mass or less, more preferably 0.8% by mass or more and 6% by mass or less, even more preferably 1% by mass or more and 5% by mass or less, and even more preferably 1% by mass or more and 3% by mass or less.

When a polyglycerol fatty acid ester and a lipophilic surfactant having an HLB of from 2 to 6 other than the polyglycerol fatty acid ester are used in combination, the content of the lipophilic surfactant having an HLB of from 2 to 6 other than the polyglycerol fatty acid ester is preferably 0.5% by mass or more, more preferably 0.8% by mass or more, and even more preferably 1% by mass or more;

preferably 8% by mass or less, more preferably 7% by mass or less, even more preferably 5% by mass or less, even more preferably 3.5% by mass or less, and even more preferably 2% by mass or less in the water-in-oil emulsion composition of the present invention from the viewpoint of improving emulsifying property, long-term storage stability, and water occlusive, adjusting the viscosity to suitable level, and obtaining a good feeling upon use without stickiness and uncomfortable feeling. The specific range is preferably 0.5% by mass or more and 8% by mass or less, more preferably 0.8% by mass or more and 7% by mass or less, even more preferably 1% by mass or more and 5% by mass or less, even more preferably 1% by mass or more and 3.5% by mass or less, and even more preferably 1% by mass or more and 2% by mass or less.

Component (B) is a dextrin fatty acid ester having 8 to 22 carbon atoms in the fatty acid moiety. By containing such a dextrin fatty acid ester, the water-in-oil emulsion composition can have improved water occlusive, and improved skin protective feeling and coverage, can be adjusted to a desired viscosity, and can be prepared with excellent storage stability. As the dextrin fatty acid ester of component (B), a dextrin fatty acid ester having 12 to 18 carbon atoms in the fatty acid moiety is preferable, a dextrin fatty acid ester having 14 to 18 carbon atoms in the fatty acid moiety is more preferable, a dextrin fatty acid ester having 14 to 16 carbon atoms in the fatty acid moiety is even more preferable, and a dextrin fatty acid ester having 16 carbon atoms in the fatty acid moiety is even more preferable. Specific examples thereof include dextrin caprylate, dextrin caprate, dextrin laurate, dextrin ethylhexanoate, dextrin myristate, dextrin palmitate, dextrin stearate, dextrin isostearate, dextrin behenate, and the like, and preferably dextrin ethylhexanoate, dextrin myristate, dextrin palmitate, and dextrin stearate more preferably dextrin myristate, and dextrin palmitate, and even more preferably dextrin palmitate; and one or more of these may be used. It should be noted that two or more of dextrin fatty acid esters prepared in advance may be used, or a mixed fatty acid dextrin ester obtained by mixing fatty acids at the time of production and then reacting with dextrin may be used.

Component (B) is contained in the water-in-oil emulsion composition of the present invention in an amount of 0.15% by mass or more and 8% by mass or less. If the content of component (B) falls within this range, sufficient water occlusive can be obtained, and the skin protective feeling and glossiness is good, and long-term storage stability is excellent. In addition, from the same viewpoint, the content of component (B) is preferably 0.2% by mass or more, more preferably 0.3% by mass or more, and even more preferably 0.4% by mass or more; preferably 6% by mass or less, more preferably 5% by mass or less, even more preferably 4% by mass or less, and even more preferably 2% by mass or less. The specific range is preferably 0.2% by mass Or more and 6% by mass or less, more preferably 0.3% by mass or more and 5% by mass or less, even more preferably 0.4% by mass or more and 4% by mass or less, and even more preferably 0.4% by mass or more and 2% by mass or less.

Component (C) is one or more oily components selected from a dimer acid ester, a fatty acid cholesterol ester having 16 to 22 carbon atoms, a fatty acid phytosterol ester having 16 to 22 carbon atoms, and an N-acyl amino acid ester. Component (C) is excellent in water-holding capacity, and by containing component (C) in a specific range, sufficient water occlusive can be obtained, and at the same time, skin protective feeling and the glossiness are good, and feeling upon use of the applied skin is good without stickiness and uncomfortable feeling.

Examples of the dimer acid ester include an ester of a dimer acid and an alcohol, preferably an ester of a dimer dilinoleic acid, and more preferably an ester of a dimer dilinoleic acid and dimer diol. The ester moiety of a dimer acid or a dimer dilinoleic acid preferably contains one or more moieties selected from behenyl, isostearyl, stearyl, cetyl, and phytosteryl, and more preferably contains two or more moieties selected from behenyl, isostearyl, stearyl, cetyl, and phytosteryl. More specifically, dimer dilinoleic acid dimer dilinoleyl bis (behenyl/isostearyl/phytosteryl), dimer dilinoleic acid dimer dilinoleyl bis (phytosteryl/isostearyl/cetyl/stearyl/behenyl), dimer dilinoleic acid (phytosteryl/isostearyl/cetyl/stearyl/behenyl), dimer dilinoleic acid di(isostearyl/phytosteryl), and dimer dilinoleyl diisosteate, preferably dimer dilinoleic acid (phytosteryl/isostearyl/cetyl/stearyl/behenyl) and dimer dilinoleic acid di(isostearyl/phytosteryl), and more preferably dimer dilinoleic acid (phytosteryl/isostearyl/cetyl/stearyl/behenyl).

Commercially available products thereof include "Plandool-S, -H" for dimer dilinoleic acid (phytosteryl/isostearyl/cetyl/stearyl/behenyl); "LUSPLAN PI-DA" for dimer dilinoleic acid di (isostearyl/phytosteryl); "LUSPLAN DD-DA" for dimer dilinoleic acid dimer dilinoleyl; "Plandool-G" for dimer dilinoleic acid dilinoleyl (behenyl/isostearyl/phytosteryl); and "LUSPLAN DD-IS" for dimer dilinoleyl diisostearate, all manufactured by Nippon Fine Chemical Co., Ltd.

Examples of the fatty acid cholesterol ester having 16 to 22 carbon atoms include cholesterol palmitate, cholesterol stearate, cholesterol behenate, cholesterol isostearat, cholesterol oleate, cholesterol palmitoleate, cholesterol behenate, cholesterol linoleate, cholesterol linolenate, and the like. The fatty acid may be a mixed fatty acid, for example, a sunflower seed oil fatty acid cholesterol ester, a macadamia nut oil fatty acid cholesterol ester, and the like. It may also contain a fatty acid cholesterol ester having a carbon number other than 16 to 22. Preferable examples thereof include cholesterol stearate, cholesterol isostearate, cholesterol oleate, cholesterol palmitoleate, cholesterol linoleate, cholesterol ester linolenate, sunflower seed oil fatty acid cholesterol ester, macadamia nut oil fatty acid cholesterol ester, and more preferable examples thereof include cholesterol isostearate.

Examples of phytosterol esters having 16 to 22 carbon atoms include phytosterol palmitate, phytosterol stearate, phytosterol behenate, phytosterol isostearate, phytosterol oleate, phytosterol palmitoleate, phytosterol behenate, phytosterol linoleate, phytosterol linolenate, and the like. The fatty acid may be a mixed fatty acid, for example, a sunflower seed oil fatty acid phytosterol ester, a macadamia nut oil fatty acid phytosterol ester, and the like. It may also contain a fatty acid phytosterol ester having a carbon number other than 16 to 22. Preferable examples thereof include phytosterol stearate, phytosterol isostearate, phytosterol oleate, phytosterol palmitoleate, phytosterol linoleate, phytosterol linolenate, sunflower seed oil fatty acid phytosterol ester, macadamia nut seed fatty acid phytosterol ester, and more preferable examples thereof include macadamia nut oil fatty acid phytosterol ester.

The number of carbon atoms of the acyl group in the N-acyl amino acid ester is preferably 10 to 30, more preferably 12 to 18. The acyl group may be saturated or unsaturated. Example thereof include preferably a 2-ethylhexanoyl group, a lauroyl group, a myristoyl group, a palmitoyl group, stearoyl group, a behenoyl group, an oleoyl group, an isostearoyl group, a linolenoyl group, or the like, more preferably a myristoyl group, or a lauroyl group, and even more preferably a lauroyl group. The acyl group may be derived from a mixed fatty acid, and preferably is a cocoyl fatty acid ester, a palm oil fatty acid ester, a palm kernel oil fatty acid ester, a sunflower seed oil fatty acid ester, or a macadamia nut oil fatty acid ester, and more preferably is a cocoyl fatty acid ester or a palm kernel oil fatty acid ester.

The N-acyl amino acid ester is preferably an alkyl ester of an N-acyl amino acid. The number of carbon atoms of the alkyl group constituting the alkyl ester is preferably 1 to 30, more preferably 12 to 18. The alkyl group may be branched, linear, or cyclic. Examples thereof include octyl, lauryl, cetyl, stearyl, isostearil, behenil, octyldodecyl, phytosteryl such as campesteryl, or sitosteryl, cholesteryl, and decyl tetradecyl.

The amino acid moiety in the N-acyl amino acid ester is an acidic amino acid, a neutral amino acid, and a basic amino acid, preferably an acidic amino acid, and a neutral amino acid, and more preferably an acidic amino acid. Specific examples thereof include glutamic acid, aspartic acid, alanine, arginine, glycine, N-methylalanine, histidine, serine, threonine, sarcosine, and the like, preferably glutamic acid, aspartic acid, alanine, N-methylalanine, and sarcosine and more preferably glutamic acid.

It is also preferred that the N-acyl amino acid ester is a diester rather than a monoester. An N-acyl lauroyl glutamic acid diester, and an N-acyl aspartic acid diester are more preferred, and an N-acyl lauroyl glutamic acid diester is more preferred. The alkyl groups present in one molecule of diester may be the same or different, but two or more are preferably present.

In the present invention, the N-acyl amino acid esters may be contained singly or in a combination of two or more of them. For example, suitable examples thereof include di (cholesteryl/behenyl/octyldodecyl) N-lauroyl-L-glutamate, di (cholesteryl/octyldodecyl) N-lauroyl-L-glutamate, di (phytosteryl/behenyl/octyldodecyl) N-lauroyl-L-glutamate, di (phytosteryl/octyldodecyl) N-lauroyl-L-glutamate, and (phytosteryl/decyltetradecyl) N-myristoyl-N-methylalaninate, more suitable examples thereof include di(cholesteryl/octyldodecyl) N-lauroyl-L-glutamate and di(phytosteryl/octyldodecyl) N-lauroyl-L-glutamate.

Commercially available products of the N-acyl amino acid ester include "ELDEW PS-203" and "Plandool-LG2 (di(phytosteryl/octyldecyl) N-lauroyl-L-glutamate), "ELDEW CL-301 (di(cholesteryl/behenyl/octyldodecyl) N-lauroyl glutamate), "ELDEW CL-202 (di(cholesteryl/octyldodecyl) N-lauroyl glutamate), "ELDEW PS-304", "ELDEW PS-306", "Plandool-LG1", "Plandool-LG3" and "Plandool-LG4 (di(phytosteryl/behenyl/octyldodecyl) N-lauroyl glutamate), "ELDEW APS-307" ((phytosteryl/decyltetradecyl) N-myristoyl-N-methylalaninate), and the like distributed by Ajinomoto Co., Inc. and Nippon Fine Chemical Co., Ltd.

These dimer acid ester, fatty acid cholesterol ester, fatty acid phytosterol ester, and N-acyl amino acid ester may be contained singly or in a combination of two or more of them, but it is preferable to be contained two or more of them in combination.

Of these oily components, one or more selected from a dimer acid ester and an N-acyl amino acid ester are preferable, one or more selected from a dimer dilinoleic acid ester and an N-acyl amino acid diester are more preferable, and one or more selected from a dimer dilinoleic acid ester and an N-acyl glutamic acid diester are even more preferable. Further, it is preferable that component (C) containing the dimer acid ester and the N-acyl amino acid ester contains two or more kinds, and it is more preferable that component (C) contains both the dimer dilinoleic acid ester and the N-acyl glutamic acid diester.

Component (C) is contained in the water-in-oil emulsion composition of the present invention in an amount of 1% by mass or more and 20% by mass or less. By setting the content to this level, excellent water occlusive, skin protective feeling and glossiness, and good feeling upon use of the applied skin without stickiness and uncomfortable feeling can be obtained. In addition, from the same viewpoint, the content of component (C) is preferably 1.5% by mass or more, more preferably 2% by mass or more, even more preferably 2.5% by mass or more, even more preferably 3% by mass or more, and even more preferably 4% by mass or more; and preferably 18% by mass or less, more preferably 16% by mass or less, even more preferably 12% by mass or less, even more preferably 9% by mass or less, and even more preferably 7% by mass or less. The specific range is preferably 1.5% by mass or more and 18% by mass or less, more preferably 2% by mass or more and 16% by mass or less, even more preferably 2% by mass or more and 12% by mass or less, even more preferably 2.5% by mass or more and 9% by mass or less, even more preferably 3% by mass or more and 9% by mass or less, and even more preferably 3% or more and 7% by mass or less.

Component (D) is a hydrocarbon oil that is liquid at 25° C. By blending component (D) and components (A) and (B) in addition to the oily component of component (C), not only the water occlusive is improved, but also protective feeling and glossiness of the skin are improved, and the long-term storage stability is also improved.

Such hydrocarbon oils include linear or branched hydrocarbon oils such as liquid paraffin, liquid isoparaffin, squalane, squalene, and the like, and are preferably squalane. One or more of them can be used.

From the viewpoint of increased water occlusive, skin protective feeling, coverage and glossiness, and good feeling upon use without stickiness and uncomfortable feeling and long-term storage stability, the content of component (D) is preferably 1% by mass or more, more preferably 3% by mass or more, even more preferably 4% by mass or more, even more preferably 5% by mass or more, and even more preferably 7% by mass or more; and preferably 30% by mass or less, more preferably 25% by mass or less, even more preferably 20% by mass or less, even more preferably 18% by mass or less, even more preferably 16% by mass or less, even more preferably 15% by mass or less, even more preferably 12% by mass or less, and even more preferably 10% by mass or less in the water-in-oil emulsion composition of the present invention. The specific range is preferably 1% by mass or more and 30% by mass or less, more preferably 3% by mass or more and 30% by mass or less, even more preferably 4% by mass or more and 25% by mass or less, even more preferably 4% by mass or more and 18% by mass or less, even more preferably 5% or more and 20% by mass or less, even more preferably 5% or more and 16% by mass or less, even more preferably 7% or more and 15% or less, even more preferably 7% or more and 12% by mass or less, and even more preferably 7% or more and 10% by mass or less.

The water-in-oil emulsion composition of the present invention contains water (E) as an aqueous phase component. From the viewpoint of water occlusive, skin protective feeling, glossiness and long-term storage stability, the content of water is preferably 10% by mass or more, more preferably 15% by mass or more, even more preferably 20% by mass or more, and preferably 65% by mass or less, more preferably 60% by mass or less, and even more preferably 50% by mass or less in the water-in-oil emulsion composition of the present invention. The specific range is preferably 10% by mass or more and 65% by mass or less, more preferably 15% by mass or more and 60% by mass or less, and even more preferably 20% by mass or more and 50% by mass or less.

It is preferable that the water-in-oil emulsion composition of the present invention further contains an oily component having a melting point of from 50 to 150° C. other than component (F) for the purpose of improving water occlusive and storage stability, and providing a good feeling upon use of the applied skin without stickiness and uncomfortable feeling.

The oily component having a melting point of from 50 to 150° C. is an oily component that is solid at normal temperature (5 to 35° C.) Examples of the solid oily component include a sphingolipid such as a ceramide and a sphingosine (including a natural product and a synthetic product); a $C_{13}$-$C_{22}$ fatty acid such as stearic acid and behenic acid; and a $C_{16}$-$C_{22}$ alcohol such as cetyl alcohol, stearyl alcohol, behenyl alcohol, batyl alcohol, and chimyl alcohol and an analogous compound thereof. In the water-in-oil emulsion composition of the present invention, when component (F) is a ceramide in particular, it is considered that crystals are present in a refined or amorphous state in the water-in-oil emulsion composition by containing a ceramide together with component (B) and component (C), thereby improving the water occlusive of a film formed at the time of application.

Examples of a ceramide include a structural analogue of ceramide described in JP-A-S62-228048, JP-A-S63-216812, JP-A-S63-227513, JP-A-S64-29347, JP-A-S64-31752, and JP-A-H8-319263, in addition to a natural ceramide and sphingosine derivative. Specifically, a compound selected from the compounds of the following formulae (1) and (2) is preferable from the viewpoint of giving coverage of the skin and glossiness to the skin.

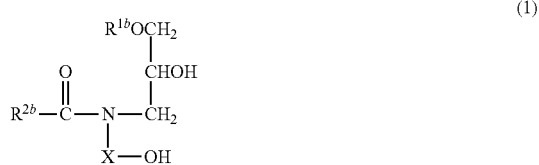

(1)

wherein $R^{1b}$ represents a hydrocarbon group having 10 to 26 carbon atoms, $R^{2b}$ represents a hydrocarbon group having 9 to 25 carbon atoms, and X represents —$(CH_2)_n$— (where n represents an integer of 2 to 6).

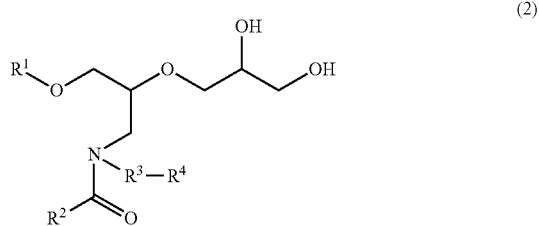

(2)

wherein $R^1$ and $R^2$ are the same or different from each other and represent an optionally hydroxylated hydrocarbon group having 1 to 40 carbon atoms, $R^3$ represents an alkylene group having 1 to 6 carbon atoms or single bonds, $R^4$ represents a hydrogen atom, an alkoxy group having 1 to 12 carbon atom, or 2,3-dihydroxypropyloxy group, (wherein $R^4$ is a hydrogen atom when $R^3$ is a single bond.)

In the above formulae (1) and (2), an alkyl group or an alkenyl group is preferable as the hydrocarbon group.

Examples of the compound of formula (1) include N-(hexadecyloxyhydroxypropyl)-N-hydroxyethylhexadecanamide, and examples of the compound of formula (2) include long chain dibasic acid bis 3-methoxypropylamide.

Among these of component (F), a ceramide (in particular, natural ceramide, a sphingosine, and a compound of the above formulae (1) and (2)), a $C_{16}$-$C_{22}$ fatty acid, and a $C_{16}$-$C_{22}$ alcohol are preferable from the viewpoint of water occlusive, skin protective feeling, and good feeling upon use of the applied skin without stickiness and uncomfortable feeling; and among them, a ceramide is more preferable, the compound of the above formula (1), and the compound of the above formula (2) are even more preferable, and the compound of the above formula (1) is even more preferable. These solid oily components can be used singly or in combination of two or more of them.

Component (F) is preferably contained in the water-in-oil emulsion composition of the present invention in an amount of 1% by mass or more and 30% by mass or less from the viewpoint of improvement in water occlusive and improvement in skin protective feeling. The content of component (F) is preferably 1.5% by mass or more, more preferably 2% by mass or more, even more preferably 3% by mass or more, and even more preferably 5% by mass or more; and preferably 20% by mass or less, more preferably 18% by mass or less, and even more preferably 16% by mass or less from the same viewpoint. The specific range is preferably 1.5% by mass or more and 20% by mass or less, more preferably 2% by mass or more and 18% by mass or less, even more preferably 3% by mass or more and 18% by mass or less, and even more preferably 5% by mass or more and 16% by mass or less.

In addition to the above components, the water-in-oil emulsion composition of the present invention may contain a liquid oil other than component (D), a humectant, a preservative, an antioxidant, a chelating agent, a perfume, and the like.

Here, examples of the liquid oil other than component (D) include silicone oil, ester oil, fluorine oil, and the like. Examples of humectant include a polyhydric alcohol such as glycerin, 1,3-butylene glycol, propylene glycol, 1,3-propanediol, dipropylene glycol, sorbitol, maltitol, mannitol, erythritol, xylitol, and trehalose, a plant extract, a betaine, POE methyl glucoside, and polyethylene glycol. As the medicinal component, either a water-soluble drug or a water-insoluble drug can be used, but specific examples thereof include allantoin, glycyrrhetinic acid salt, glycyrrhetinic acid, glycyrrhetinic acid ester such as stearyl glycyrrhetinate, isopropylmethylphenol, a retinol derivative, an anti-wrinkling agent, whitening agent, a fungicide, a plant extract, tocopherol acetate, a vitamin, salicylic acid, indomethacin, and the like; and other medicinal component used in a cosmetic, a quasi-drug, and a pharmaceutical can be used also.

The water-in-oil emulsion composition of the present invention may be water-in-oil type and in a form that can be easily applied to the skin, and the viscosity thereof at 25° C. is preferably 15 Pa·s or more, more preferably 20 Pa·s or more, even more preferably 25 Pa·s or more, and even more preferably 30 Pa·s or more; and preferably 5000 Pa·s or less, more preferably 1000 Pa·s or less, even more preferably 500 Pa·s or less, even more preferably 300 Pa·s or less, and even more preferably 150 Pa·s or less. The specific range is preferably 15 Pa·s or more and 5000 Pa·s or less resulting in cream form, more preferably 20 Pa·s or more and 1000 Pa·s or less resulting in cream form, even more preferably 20 Pa·s or more and 500 Pa·s or less resulting in a cream form, even more preferably 25 Pa·s or more and 300 Pa·s or less resulting in a cream form, and even more preferably 30 Pa·s or more and 150 Pa·s or less resulting in a cream form. Here, the viscosity at 25° C. can be measured by using B8R type viscometer, under a condition of minute and 25° C.

In the water-in-oil emulsion composition of the present invention, for example, oily components (water-insoluble components) are mixed by heating and stirring, and then water-soluble components are mixed by heating and stirring according to a conventional method. The water-oil emulsion composition can be prepared by adding the mixture of the water-soluble components to the mixture of the oily components, mixing the resulting mixture, stirring the mixture thoroughly with homogenizer, and then cooling the mixture. As the temperature, it is preferable to obtain a water-in-oil emulsified composition by stirring and emulsifying with a homogenizer at a temperature equal to or higher than a melting point of the oily components (water-insoluble components) and then cooling.

The use of the water-in-oil emulsion composition of the present invention is not particularly limited, but is preferably application to the hair and/or skin, and is more preferably application to the skin of face, body, limb, and the like. It is also preferably used as a skin external preparation, and more preferably as a skin cosmetic. The method of use is not particularly limited, but it is preferably applied to the hair and/or skin by hand or tool, and more preferably to the skin by hand or tool.

With respect to the above-described embodiments, the present invention further discloses the following compositions.

<1> A water-in-oil emulsion composition comprising the following components (A), (B), (C), (D) and (E):
 (A) 1% by mass or more and 15% by mass or less of a lipophilic surfactant having an HLB of from 2 to 6;
 (B) 0.15% by mass or more and 8% by mass or less of a dextrin fatty acid ester having 8 to 22 carbon atoms in the fatty acid moiety;
 (C) 1% by mass or more and 20% by mass or less of one or more oily components selected from the group consisting of a dimer acid ester, a fatty acid cholesterol ester having 16 to 22 carbon atoms, a fatty acid phytosterol ester having 16 to 22 carbon atoms and an N-acyl amino acid ester,
 (D) a hydrocarbon oil that is liquid at 25° C., and
 (E) water.

<2> The water-in-oil emulsion composition according to <1>, wherein component (A) is preferably a nonionic surfactant having an HLB of from 2 to 6, more preferably one or more selected from the group consisting of a glycerol fatty acid ester, a polyglycerol fatty acid ester, a propylene glycol fatty acid ester, a sorbitan fatty acid ester, a polyoxyethylene castor oil, a polyoxyethylene hydrogenated castor oil, a polyoxyethylene hydrogenated castor oil fatty acid ester, a polyethylene glycol fatty acid ester, an alkyl glyceryl ether, an alkyl polyglyceryl ether, a polyoxyethylene alkyl ether, polyoxyethylene alkyl ether fatty acid ester, a polyoxyethylene alkyl amine, and a silicone surfactant; even more preferably polyoxyethylene hydrogenated castor oil, an alkyl glyceryl ether, polyglycerol fatty acid ester, a polyether modified silicone having a linear silicone chain, and a polyether modified silicone having a branched silicone chain, even more preferably an alkyl glyceryl ether, a polyglycerol fatty acid ester, and a polyether modified silicone having a linear silicone chain.

<3> The water-in-oil emulsion composition according to <1> or <2>, wherein the content of component (A) is preferably 1.5% by mass or more, more preferably 2% by mass or more, and even more preferably 2.5% by mass or more; and preferably 12% by mass or less, more preferably 10% by mass or less, even more preferably 8% by mass or less, even more preferably 6% by mass or less, even more preferably 5% by mass or less, and even more preferably 4.5% by mass or less in the water-in-oil emulsion composition.

<4> The water-in-oil emulsion composition according to any one of <1> to <3>, wherein component (B) is preferably a dextrin fatty acid ester having 12 to 18 carbon atoms in the fatty acid moiety, more preferably a dextrin fatty acid ester having 14 to 18 carbon atoms in the fatty acid moiety, even more preferably a dextrin fatty acid ester having 14 to 16 carbon atoms in the fatty acid moiety, and even more preferably a dextrin fatty acid ester having 16 carbon atoms in the fatty acid moiety.

<5> The water-in-oil emulsion composition according to any one of <1> to <4>, wherein the content of component (B) is preferably 0.2% by mass or more, more preferably 0.3% by mass or more, and even more preferably 0.4% by mass or more; and preferably 6% by mass or less, more preferably 5% by mass or less, even more preferably 4% by mass or less, and even more preferably 2% by mass or less in the water-in-oil emulsion composition.

<6> The water-in-oil emulsion composition according to any one of <1> to <5>, wherein component (C) is preferably one or more selected from the group consisting of a dimer acid ester and an N-acyl amino acid ester, more preferably one or more selected from the group consisting of a dimer dilinoleic acid ester and an N-acyl amino acid diester, and even more preferably one or more selected from the group consisting of a dimer dilinoleic acid ester and an N-acyl glutamic acid diester.

<7> The water-in-oil emulsion composition according to any one of <1> to <6>, wherein the content of component (C) is preferably 1.5% by mass or more, more preferably 2% by mass or more, even more preferably 3% by mass or more, and even more preferably 4% by mass or more; and preferably 18% by mass or less, more preferably 16% by mass or less, even more preferably 12% by mass or less, even more preferably 9% by mass or less, and even more preferably 7% by mass or less in the water-in-oil emulsion composition.

<8> The water-in-oil emulsion composition according to any one of <1> to <7>, wherein component (D) is preferably a linear or paraffin, liquid isoparaffin, squalane, and squalene, and more preferably is squalane.

<9> The water-in-oil emulsion composition according to any one of <1> to <8>, wherein the content of component (D) is preferably 3% by mass or more, more preferably 4% by mass or more, even more preferably 5% by mass or more, and even more preferably 7% by mass or more; and preferably 30% by mass or less, more preferably 25% by mass or less, even more preferably 20% by mass or less, even more preferably 15% by mass or less, and even more preferably 10% by mass or less in the water-in-oil emulsion composition.

<10> The water-in-oil emulsion composition according to any one of <1> to <9>, wherein the content of component (E) is preferably 10% by mass or more, more preferably 15% by mass or more, and even more preferably 20% by mass; and preferably 65% by mass or less, more preferably 60% by mass or less, and even more preferably 50% by mass or less.

<11> The water-in-oil emulsion composition according to any one of <1> to <10>, wherein the composition further comprises (F) an oily component having melting point of from 50 to 150° C., preferably one or more selected from the group consisting of a sphingolipid such as a ceramide and a sphingosine (including a natural product and a synthetic product); a $C_{13}$-$C_{22}$ fatty acid such as stearic acid and behenic acid; a $C_{16}$-$C_{22}$ alcohol such as cetyl alcohol, stearyl alcohol, behenyl alcohol, batyl alcohol, and kimyl alcohol; and an analogous compound thereof.

<12> The water-in-oil emulsion composition according to any one of <1> to <11>, wherein component (F) is preferably a ceramide (in particular, a natural ceramide, a sphingosine, a compound of the above formulae (1) and (2)), a $C_{16}$-$C_{22}$ fatty acid, and a $C_{16}$-$C_{22}$ alcohol; and among these, even more preferably a ceramide, even more preferably a component of the above formula (1) and a compound of the above formula (2), and even more preferably a compound of the above formula (1).

<13> The water-in-oil emulsion composition according to <11> or <12>, wherein the content of component (F) is 1% by mass or more and 30% by mass; preferably 1.5% by mass or more, more preferably 2% by mass or more, and even more preferably 3% by mass or more, even more preferably 5% by mass or more; and preferably 20% by mass or more, more preferably 18% by mass or less, and even more preferably 16% by mass or less in the water-in-oil emulsion composition.

<14> The water-in-oil emulsion composition according to any one of <1> to <13>, wherein the viscosity thereof at 25° C. is preferably 15 Pa·s or more, more preferably 20 Pa·s or more, and even more preferably 25 Pa·s or more; and preferably 5000 Pa·s or less, more preferably 1000 Pa·s or less, even more preferably 500 Pa·s or less, and even more preferably 300 Pa·s or less.

<15> A water-in-oil emulsion composition comprising the following components (A), (B), (C), (D), (E) and (F):

(A) 1% by mass or more and IS % by mass or less of a polyether modified silicone having an HLB of from 2 to 6;

(B) 0.15% by mass or more and 8% by mass or less of a dextrin fatty acid ester having 12 to 18 carbon atoms in the fatty acid moiety;

(C) 1% by mass or more and 20% by mass or less of one or more oily components selected from the group consisting of a dimer acid ester, a fatty acid cholesterol ester having 16 to 22 carbon atoms, a fatty acid phytosterol ester having 16 to 22 carbon atoms, and an N-acyl amino acid ester;

(D) an oily component that is liquid at 25° C.;

(E) water; and (F) a ceramide.

<16> The water-in-oil emulsion composition according to <15>, wherein component (C) is one or more selected from dimer dilinolic acid ester and N-acyl amino acid diester.

<17> The water-in-oil emulsion composition according to <15> or <16>, wherein component (D) is squalane.

<18> The water-in-oil emulsion composition according to any one of <15> to <17>, wherein component (F) is a compound of the above formula (1).

<19> The water-in-oil emulsion composition according to any one of <1> to <18>, wherein the composition is a skin external preparation, preferably a skin cosmetic.

<20> A method of using the water-in-oil emulsion composition according to any one of <1> to <19>, comprising: applying the water-excluding hair, preferably any of the face, body, or limb.

EXAMPLES

Next, the present invention will be described in more detail with reference to Examples and Comparative Examples.

Examples 1 to 23 and Comparative Examples 1 to 6

Water-in-oil emulsion compositions were prepared using the ingredients shown in Tables 1 to 6. That is, the oily components (water-insoluble components) were stirred and mixed at 80 to 85° C., and then the water-soluble components were stirred and mixed at 80 to 85° C. The mixture of the above water-soluble components was added to the mixture of the above oily components and mixed, and thoroughly stirred with a homogenizer at 80 to 85° C., followed by cooling to thereby obtain water-in-oil emulsion composition.

The resulting water-in-oil emulsion composition was evaluated for water occlusive (water evaporation suppression rate), skin skin glossiness (glossy skin), and a feeling of the applied skin without stickiness and uncomfortable feeling according to the following evaluation method. Storage stability was also evaluated.

The evaluation results are shown in Tables 1 to 6.

(1) Water Evaporation Suppression Rate

Filter paper (No. 5B, 21-mm diameter, manufactured by ADVANTEC Corporation)

Pierce Vial CV-400 (product distributed by AS ONE Corporation, product code 5-106-06, inner diameter×barrel diameter×overall height: φ17×φ27×95 mm, volume: 40 mL)

Calcium chloride (for drying): manufactured by Junsei Chemical Co., Ltd.

Desiccator

Microman (Gilson Incorporated.)

(i) The resin lid attached to the screw cap of the Pierce Vial was removed.

(ii) The prepared water-in-oil emulsion composition was placed in an amount of 0.03 mL using Microman on a filter paper, and uniformly applied to one side of the filter paper with a spatula.

(iii) The filter paper was placed in the screw cap such that the surface applied with the water-in-oil emulsion composition was contacted with the inner surface of the screw cap of the Pierce Vial. A sample of only the filter paper to which the water-in-oil emulsion composition was not applied was also prepared.

(iv) The Pierce Vial was filled with 10 mL of distilled water, closed with the screw cap in which the filter paper prepared in (iii) was placed, and used as a sample.

(v) The weight of the sample (=total weight of preparation-applied filter paper, screw cap, vial, water) was measured with an electronic balance.

(vi) Calcium chloride (for drying) was placed in a desiccator, the sample was placed in the desiccator, a lid was put thereon, and the desiccator was left to stand at 20° C. for 5 days. At this time, 5RH % was kept in the desiccator.

(vii) The sample was taken out of the desiccator and the weight of the sample (=total weight of formulation-applied filter paper, screw cap, vial, water) was measured.
(viii) Three samples were prepared for each of Examples and Comparative Examples. Three samples were also prepared for filter paper to which nothing was applied.
(ix) The water evaporation amount was measured, and the water evaporation suppression rate of the water-in-oil emulsion composition shown in Examples and Comparative Examples was calculated.

Water evaporation ($W_a$) of sample applied with water-in-oil emulsion composition=(sample weight after drying for 5 days)−(sample weight prior to drying)

$W_a$ mean=($W_{a1}$+$W_{a2}$+$W_{a3}$)/3

Water evaporation ($W_0$) of sample not applied with water-in-oil emulsion composition=(sample weight after drying for 5 days)−(sample weight prior to drying)

$W_0$ mean=($W_{01}$+$W_{02}$+$W_{03}$)/3

Water evaporation suppression rate (%)=(($W_0$ mean−$W_a$ mean)/$W_0$ mean)×100

(2) Protective Feeling of the Skin and Glossiness of the Skin

The water-in-oil emulsion compositions of Examples and Comparative Examples were evaluated according to the following methods of use by four expert panelists.
(i) Expert panelists washed his/her face with a commercially available Curel-moisturizing foam face wash manufactured by Kao Corporation and wiped it with a towel.
(ii) The water-in-oil emulsion composition was taken with fingers at 0.05 g and spread over the entire face.
(iii) Ten minutes after application, the expert panelists evaluated the skin protective feeling on the basis of the following criteria, and the average score of four panelists was obtained. In addition, expert panelists looked at the mirror in a room with a constant brightness to evaluate the texture of the skin on the basis of the following criteria, and the average score of four panelists was obtained.
(Skin Protective Feeling)
5: The skin feels very covered.
4: Felt the skin covered.
3: Slightly felt the skin covered.
2: Hardly felt the skin covered.
1: Not felt the skin covered at all.
(Skin Glossiness)
5: Very glossy.
4: Glossy.
3: Slightly glossy.
2: Less glossy.
1: Not glossy.
(3) No Stickiness and No Uncomfortable Feeling The water-in-oil emulsion compositions of Examples and Comparative Examples were evaluated according to the following methods of use by four expert panelists.
(i) Expert panelists washed his/her face with commercially available Curel-moisturizing foam face wash manufactured by Kao Corporation and wiped it with a towel.
(ii) The water-in-oil emulsion composition was taken with fingers at 0.05 g and spread over the entire face.
(iii) Three hours after application, expert panelists evaluated the feeling of burden on the skin on the basis of the following criteria, and the average score of four panelists was obtained.
5: No stickiness and no uncomfortable feeling.
4: Almost no stickiness and no uncomfortable feeling.
3: Not much stickiness and not much uncomfortable feeling.
2: Sticky and slight uncomfortable feeling.
1: Very sticky and uncomfortable feeling.
(4) Storage Stability The water-in-oil compositions of the Examples and Comparative Examples were placed in a 110 mL transparent glass container (standard bottle #11, Tokyo Garasu Kikai Co., Ltd.) in a volume of 80 mL, sealed, and stored at room temperature for a certain period of time. The appearance of these water-in-oil compositions after storage was visually determined on the basis of the following criteria.
A: A uniform single layer and not observed separation of aqueous or oily components. Creamy.
B: Observed partial separation of aqueous and oily components, but maintained creamy as a whole.
C: Entire separation of aqueous and the oily components and not maintained creamy as a whole.
(4) Viscosity Using a TVB-10 viscometer manufactured by Toki Sangyo Co., Ltd., the viscosity was measured under the condition of rotors: T-C, rotational speeds: 5 rpm, measurement time: 1 minute, and measurement temperature: 25° C.

TABLE 1

| Component | Component name | Example: 1 | 2 | 3 | 4 | 5 | 6 |
|---|---|---|---|---|---|---|---|
| | Allantoin | 0.5 | 0.5 | 0.5 | 0.5 | 0.5 | 0.5 |
| (F) | N-(hexadecyloxyhydroxypropyl)-N-hydroxyethylhexadecanamide *1 | 8.0 | | 3.0 | | | 15.0 |
| | Stearic acid | | | | | 6.0 | |
| | Stearyl alcohol | | | | 6.0 | | |
| (A) | Isostearyl glyceryl ether *2 | 0.2 | 0.2 | 0.2 | 0.2 | 0.2 | 0.2 |
| | Polyoxyethylene/methylpolysiloxane copolymer *3 | 1.5 | | 1.5 | 1.5 | 1.5 | 1.5 |
| | Polyoxyethylene/methylpolysiloxane copolymer *4 | | 1.5 | | | | |
| | Polyglyceryl diisostearate *5 | 2.0 | 2.0 | 2.0 | 2.0 | 2.0 | 2.0 |
| (D) | Squalane | 8.0 | 8.0 | 8.0 | 8.0 | 8.0 | 8.0 |
| | Methylpolysiloxane *6 | 8.0 | 8.0 | 6.0 | 8.0 | 8.0 | 8.0 |
| | Methylpolysiloxane *7 | 4.0 | 4.0 | 4.0 | 4.0 | 4.0 | 4.0 |
| | Methylpolysiloxane-crosslinked methylpolysiloxane mixture *8 | 5.0 | 5.0 | 5.0 | 5.0 | 5.0 | 5.0 |

TABLE 1-continued

| Component | Component name | Example: 1 | 2 | 3 | 4 | 5 | 6 |
|---|---|---|---|---|---|---|---|
| (C) | Di(cholesteryl octyldodecyl) N-lauroyl-L-glutamate *9 | 1.0 | 1.0 | 1.0 | 1.0 | 1.0 | 1.0 |
| | Di(phytosteryl/2-octyldodecyl) N-lauroyl-L-glutamate *10 | 2.0 | 2.0 | 2.0 | 2.0 | 2.0 | 2.0 |
| | Dimer dilinoleic acid (phytosteryl/isostearyl/cetyl/stearyl/bchenyl)*11 | 2.5 | 2.5 | 2.5 | 2.5 | 2.5 | 2.5 |
| (B) | Dextrin palmitate *12 | 0.5 | 4.0 | 0.5 | 0.5 | 0.5 | 0.5 |
| | Magnesium sulfate heptahydrate | 0.7 | 0.7 | 0.7 | 0.7 | 0.7 | 0.7 |
| | Glycerin (86%) | 10.0 | 10.0 | 10.0 | 10.0 | 10.0 | 10.0 |
| | 1,3-Butylene glycol | 4.0 | 4.0 | 4.0 | 4.0 | 4.0 | 4.0 |
| | Eucalyptus extract | 0.33 | 0.33 | 0.33 | 0.33 | 0.33 | 0.33 |
| | Water-soluble ginger extract (K) | 0.5 | 0.5 | 0.5 | 0.5 | 0.5 | 0.5 |
| | Hiba arborvitae extract | 2.0 | 2.0 | 2.0 | 2.0 | 2.0 | 2.0 |
| | Methylparaben | 0.33 | 0.33 | 0.33 | 0.33 | 0.33 | 0.33 |
| | Succinic acid | 0.1 | 0.1 | 0.1 | 0.1 | 0.1 | 0.1 |
| | Sodium hydroxide solution (48%) | 0.07 | 0.07 | 0.07 | 0.07 | 0.07 | 0.07 |
| (E) | Water | 38.77 | 43.27 | 43.77 | 40.77 | 40.77 | 31.77 |
| | Total | 100.0 | 100.0 | 100.0 | 100.0 | 100.0 | 100.0 |
| | Component (A) | 3.7 | 3.7 | 3.7 | 3.7 | 3.7 | 3.7 |
| | Component (B) | 0.5 | 4.0 | 0.5 | 0.5 | 0.5 | 0.5 |
| | Component (C) | 5.5 | 5.5 | 5.5 | 5.5 | 5.5 | 5.5 |
| | Component (D) | 8.0 | 8.0 | 8.0 | 8.0 | 8.0 | 8.0 |
| | Component (E) | 38.77 | 43.27 | 43.77 | 40.77 | 40.77 | 31.77 |
| | Component (F) | 8.0 | 0.0 | 3.0 | 6.0 | 6.0 | 15.0 |
| | Viscosity (Pa · s) | 48 | 122 | 45 | 38 | 40 | 120 |
| Evaluation | Water evaporation suppression rate (%) | 49 | 12 | 27 | 18 | 12 | 52 |
| | Skin-covering feeling | 5.0 | 2.5 | 3.5 | 3.0 | 2.8 | 5.0 |
| | Glossiness of skin | 5.0 | 5.0 | 5.0 | 5.0 | 5.0 | 5.0 |
| | No stickiness and no uncomfortable feeling | 5.0 | 3.3 | 4.5 | 2.8 | 2.5 | 5.0 |
| | Storage stability (room temperature, 1 day) | A | A | A | A | A | A |
| | Storage stability (room temperature, 1 month) | A | A | A | A | A | A |

*1 Sphingolipid E (Kao Corporation)
*2 GE-IS (U) (HLB 2) (Kao Corporation)
*3 Silicone KF-6015(PEG-3 dimethicone, HLB 4.5 (Shin-Etsu Chemical Co., Ltd.)
*4 Silicone KF-6017 (PEG-10 dimethicone, HLB (Shin-Etsu Chemical Co., Ltd.)
*5 Cosmol 42V (polyglyceryl-2 diisostearate, HLB4) (Nisshin Oilio Group Ltd.)
*6 Silicone KF-96A-2CS (Shin-Etsu Chemical Co., Ltd.)
*7 Silicone KF-96A-6CS (Shin-Etsu Chemical Co., Ltd.)
*8 Silicone KSG-16 (Shin-Etsu Chemical Co., Ltd.)
*9 ELDEW CL-202 (Ajinomoto Co., Inc.)
*10 ELDEW P5-203 (Ajinomoto Co., Inc.)
*11 Plandool-H (Nippon Fine Chemical Co., Ltd.)
*12 Rheopearl KL2 (Chiba Flour Milling Co., Ltd.)

TABLE 2

| Component | Component name | Example: 7 | 8 | 9 | 10 | Comparative example 1 |
|---|---|---|---|---|---|---|
| | Allantoin | 0.5 | 0.5 | 0.5 | 0.5 | 0.5 |
| (F) | N-(hexadecyloxyhydroxypropyl)-N-hydroxyethylhexadecanamide *1 | 8.0 | 8.0 | 8.0 | 8.0 | 8.0 |
| (A) | Isostearyl glyceryl ether *2 | 0.2 | 0.2 | 0.2 | 0.2 | 0.2 |
| | Polyoxyethylene/methylpolysiloxane copolymer *3 | 1.5 | | 1.5 | 1.5 | 1.5 |
| | Polyoxyethylene/methylpolysiloxane copolymer *4 | | 2.5 | | | |
| | Polyglyceryl diisostearate *5 | 2.0 | 2.0 | 2.0 | 2.0 | |
| (D) | Squalane | 8.0 | 10.0 | 8.0 | 8.0 | 8.0 |
| | Methylpolysiloxane *6 | 8.0 | | 8.0 | 8.0 | 8.0 |
| | Methylpolysiloxane *7 | 4.0 | 6.0 | 4.0 | 4.0 | 4.0 |
| | Methylpolysiloxane-crosslinked methylpolysiloxane mixture *8 | 5.0 | 5.0 | 5.0 | 5.0 | 5.0 |

TABLE 2-continued

| Component | Component name | Example: 7 | Example: 8 | Example: 9 | Example: 10 | Comparative example 1 |
|---|---|---|---|---|---|---|
| (C) | Di(cholesteryl octyldodecyl) N-lauroyl-L-glutamate *9 | 1.0 | 2.0 | | | |
| | Di(phytosteryl/2-octyldodecyl) N-lauroyl-L-glutamate *10 | 2.0 | | | | |
| | Dimer dilinoleic acid (phytosteryl/isostearyl/cetyl/stearyl/bchenyl)*11 | | 6.0 | | | |
| | Macadamia nut oil fatty acid phytosteryl *12 | | | 5.5 | | |
| | Cholesteryl Isostearate *13 | | | | 5.5 | |
| (B) | Dextrin palmitate *14 | 0.5 | 1.0 | 0.5 | 0.5 | 0.5 |
| | Magnesium sulfate heptahydrate | 0.7 | 0.3 | 0.7 | 0.7 | 0.7 |
| | Glycerin (86%) | 10.0 | 20.0 | 10.0 | 10.0 | 10.0 |
| | Eucalyptus extract | 0.33 | 0.33 | 0.33 | 0.33 | 0.33 |
| | Water-soluble ginger extract (K) | 0.5 | 0.5 | 0.5 | 0.5 | 0.5 |
| | Horse chestnut extract extract | | 3.0 | | | |
| | Hiba arborvitae extract | 2.0 | 4.0 | 2.0 | 2.0 | 2.0 |
| | 1,3-Butylene glycol | 4.0 | | 4.0 | 4.0 | 4.0 |
| | Methylparaben | 0.33 | 0.2 | 0.33 | 0.33 | 0.33 |
| | Succinic acid | 0.1 | 0.1 | 0.1 | 0.1 | 0.1 |
| | Sodium hydroxide solution (48%) | 0.07 | 0.07 | 0.07 | 0.07 | 0.07 |
| (E) | Water | 41.27 | 28.3 | 38.77 | 38.77 | 46.27 |
| | Total | 100.0 | 100.0 | 100.0 | 100.0 | 100.0 |
| | Component (A) | 3.7 | 4.7 | 3.7 | 3.7 | 1.7 |
| | Component (B) | 0.5 | 1.0 | 0.5 | 0.5 | 0.5 |
| | Component (C) | 3.0 | 8.0 | 5.5 | 5.5 | 0.0 |
| | Component (D) | 8.0 | 0.0 | 3.0 | 8.0 | 8.0 |
| | Component (E) | 41.27 | 28.3 | 38.77 | 38.77 | 46.27 |
| | Component (F) | 8.0 | 8.0 | 8.0 | 8.0 | 8.0 |
| | Viscosity (Pa · s) | 57 | 280 | 50 | 35 | 86 |
| Evaluation | Water evaporation suppression rate (%) | 48 | 45 | 40 | 36 | 33 |
| | Skin-covering feeling | 5.0 | 5.0 | 4.3 | 3.8 | 4.0 |
| | Glossiness of skin | 4.0 | 5.0 | 4.0 | 4.0 | 1.3 |
| | No stickiness and no uncomfortable feeling | 5.0 | 3.5 | 5.0 | 5.0 | 5.0 |
| | Storage stability (room temperature, 1 day) | A | A | A | A | A |
| | Storage stability (room temperature, 1 month) | A | A | A | A | A |

*1 Sphingolipid E (Kao Corporation)
*2 GE-IS (U) (HLB 2) (Kao Corporation)
*3 Silicone KF-6015 (PEG-3 dimethicone, HLB 4.5 (Shin-Etsu Chemical Co., Ltd.)
*4 Silicone KF-6017P (PEG-10 dimethicone, HLB 4.5 (Shin-Etsu Chemical Co., Ltd.)
*5 Cosmol 42V (polyglyceryl-2 diisostearate, HLB 4) (Nisshin Oilio Group Ltd.)
*6 Silicone KF-96A-2CS (Shin-Etsu Chemical Co., Ltd.)
*7 Silicone KF-96A-6CS (Shin-Etsu Chemical Co., Ltd.)
*8 Silicone KSG-16 (Shin-Etsu Chemical Co., Ltd.)
*9 ELDEW CL-202 (Ajinomoto Co., Inc.)
*10 ELDEW PS-203 (Ajinomoto Co., Inc.)
*11 Plandool-H (Nippon Fine Chemical Co., Ltd.)
*12 Plandool-MAS (Nippon Fine Chemical Co., Ltd.)
*13 Exepearl IS-CE-A (Kao Coporation)
*14 Rheopearl KL2 (Chiba Flour Milling Co., Ltd.)

TABLE 3

| Component | Component name | Example 11 | Example 12 | Example 13 | Example 14 | Comparative example 2 | Comparative example 3 | Comparative example 4 |
|---|---|---|---|---|---|---|---|---|
| | Allantoin | 0.5 | 0.5 | 0.5 | 0.5 | 0.5 | 0.5 | 0.5 |
| (F) | N-(hexadecyloxyhydroxypropyl)-N-hydroxyethylhexadecanamide *1 | 8.0 | 3.0 | 8.0 | 8.0 | 8.0 | 8.0 | 8.0 |
| | Long-chain dibasic acid bis-3-methoxypropylamide *2 | | | | | 1.0 | | |

TABLE 3-continued

|  |  | Example | | | | Comparative example | | |
| --- | --- | --- | --- | --- | --- | --- | --- | --- |
| Component | Component name | 11 | 12 | 13 | 14 | 2 | 3 | 4 |
| (A) | Isostearyl glycery ether *3 | 0.2 | 0.2 | 0.2 | 0.2 | 2.0 | 0.2 | 0.2 |
|  | Polyoxyethylene/methylpolysiloxane copolymer *4 |  |  |  |  |  | 0.2 | 0.2 |
|  | Polyoxyethylene/methylpolysiloxane copolymer *5 |  |  |  |  |  |  | 1.5 |
|  | Polyoxyethylene/methylpolysiloxane copolymer *6 | 1.5 | 1.5 | 1.5 | 1.5 |  | 1.5 |  |
|  | Polyglyceryl diisostearate *7 | 2.0 | 2.0 | 2.0 | 2.0 | 2.0 |  |  |
|  | Polyoxyethylene hydrogenated castor oil *8 |  |  |  |  | 0.5 |  |  |
| (D) | Squalane | 8.0 | 8.0 | 8.0 | 8.0 | 3.5 | 6.0 | 6.0 |
|  | Methylcyclopolysiloxane *9 |  |  |  |  | 8.0 | 8.0 | 8.0 |
|  | Octamethyltrisiloxane *10 |  |  |  |  | 3.5 | 5.0 | 5.0 |
|  | Methylpolysiloxane *11 | 8.0 | 8.0 | 8.0 | 8.0 | 2.0 | 2.0 | 2.0 |
|  | Methylpolysiloxane *12 | 4.0 | 4.0 | 4.0 | 4.0 |  |  |  |
|  | Methylpolysiloxane-crosslink methylpolysiloxane mixture *13 | 5.0 | 5.0 | 5.0 | 5.0 |  |  |  |
|  | Dimethyl palmityl polysiloxane *14 |  |  |  |  | 0.5 |  |  |
| (C) | Chlesteryl isostearate *15 |  |  |  |  | 1.0 |  |  |
|  | Dimer dilinoleic acid (phytosteryl/isostearyl/cetyl/ stearyl/bchenyl)*11 | 2.5 | 2.5 | 2.5 | 2.5 |  |  | 3.0 |
|  | N-lauroyl-L-glutamate di(cholesteryl octyldodecyl) *17 | 1.0 | 1.0 | 1.0 | 1.0 |  |  |  |
|  | N-lauroyl-L-glutamate di(phytosteryl, 2-octyldodecyl) *18 | 2.0 | 2.0 | 2.0 | 2.0 |  |  |  |
| (B) | Dextrin palmitate *19 | 1.5 | 4.0 |  | 0.25 | 0.1 |  |  |
|  | Dextrin myristate *20 |  |  | 0.5 |  |  |  |  |
|  | Magnesium sulfate heptahydrate | 0.7 | 0.7 | 0.7 | 0.7 | 0.5 | 0.3 | 0.3 |
|  | Glycerin (86%) | 10.0 | 10.0 | 10.0 | 10.0 | 15.0 | 15.0 | 15.0 |
|  | Eucalyptus extract |  |  |  |  | 0.5 | 0.5 |  |
|  | Eucalyptus extract | 0.33 | 0.33 | 0.33 | 0.33 |  |  | 0.33 |
|  | Water-soluble ginger extract (K) | 0.5 | 0.5 | 0.5 | 0.5 |  |  | 0.5 |
|  | Horse chestnut extract |  |  |  |  |  |  | 3.0 |
|  | Hiba arborvitae extract | 2.0 | 2.0 | 2.0 | 2.0 |  |  | 4.0 |
|  | 1,3-Butylene glycol | 4.0 | 4.0 | 4.0 | 4.0 |  |  |  |
|  | Methylparaben | 0.33 | 0.33 | 0.33 | 0.33 | 0.3 | 0.2 | 0.2 |
|  | Succinic acid | 0.1 | 0.1 | 0.1 | 0.1 | 0.24 | 0.1 | 0.1 |
|  | Sodium hydroxide solution (48%) | 0.07 | 0.07 | 0.07 | 0.07 | 0.07 | 0.07 | 0.07 |
| (E) | Water | 37.77 | 40.27 | 38.77 | 39.02 | 50.59 | 52.43 | 42.3 |
|  | Total | 100.0 | 100.0 | 100.0 | 100.0 | 100.0 | 100.0 | 100.0 |
|  | Component (A) | 3.7 | 3.7 | 3.7 | 3.7 | 4.7 | 1.9 | 1.7 |
|  | Component (B) | 1.5 | 4.0 | 0.5 | 0.25 | 0.1 | 0.0 | 0.0 |
|  | Component (C) | 5.5 | 5.5 | 5.5 | 5.5 | 1.0 | 0.0 | 3.0 |
|  | Component (D) | 8.0 | 8.0 | 8.0 | 8.0 | 3.5 | 6.0 | 6.0 |
|  | Component (E) | 37.77 | 40.27 | 38.77 | 39.02 | 50.59 | 52.43 | 42.3 |
|  | Component (F) | 8.0 | 3.0 | 8.0 | 8.0 | 9.0 | 8.0 | 8.0 |
|  | Viscosity (Pa · s) | 84 | 50 | 56 | 45 | 85 | 50 | 99 |

TABLE 3-continued

|  |  | Example | | | | Comparative example | | |
| --- | --- | --- | --- | --- | --- | --- | --- | --- |
| Component | Component name | 11 | 12 | 13 | 14 | 2 | 3 | 4 |
| Evaluation | Water evaporation suppression rate (%) | 44 | 55 | 49 | 43 | 5.0 | 3.0 | 9.0 |
|  | Skin-covering feeling | 4.8 | 5.0 | 5.0 | 4.5 | 2.0 | 1.3 | 2.3 |
|  | Glossiness of skin | 5.0 | 5.0 | 5.0 | 5.0 | 2.5 | 1.3 | 3.8 |
|  | No stickiness and no uncomfortable feeling | 3.8 | 2.8 | 4.8 | 5.0 | 5.0 | 5.0 | 4.0 |
|  | Storage stability (room temperature, 1 day) | A | A | A | A | A | A | A |
|  | Storage stability (room temperature, 1 month) | A | A | A | A | A | A | A |

*1 Sphingolipid E (Kao Corporation)
*2 BRS661-C (Kao Corporation)
*3 GE-IS (U) (HLB 2) (Kao Corporation)
*4 Silicone SH3775M (PEG-12 dimethicone, HLB (Dow Corning Toray Co., Ltd)
*5 Silicone KF-6017 (PEG-10 dimethicone, HLB (Shin-Etsu Chemical Co., Ltd.)
*6 Silicone KF-6015 (PEG-3 dimethicone, HLB 4.5 (Shin-Etsu Chemical Co., Ltd.)
*7 Cosmol 42V (polyglyceryl-2 diisostearate, HLB 4) (Nisshin Oilio Group Ltd.)
*8 EMALEX HC-5K (PEG-5 hydrogenated castor oil, HLB 5 (Nippon Emulsion Co., Ltd.)
*9 Silicone TSF405A (Momentive Performance Materials Japan Inc.)
*10 Silicone KF-96A-1CS (Shin-Etsu Chemical Co., Ltd.)
*11 Silicone KF-96A-2CS (Shin-Etsu Chemical Co., Ltd.)
*12 Silicone KF-96A-6CS (Shin-Etsu Chemical Co., Ltd.)
*13 Silicone KSG-16 (Shin-Etsu Chemical Co., Ltd.)
*14 Silicone KT-16 (Momentive Performance Materials Japan Inc.)
*15 Exepearl IS-CE-A (Kao Corporation)
*16 Plandool-H (Nippon Fine Chemical Co., Ltd.)
*17 ELDEW CL-202 (Ajinomoto Co., Inc.)
*18 ELDEW PS-203 (Alinomoto Co., Inc.)
*19 Rheopearl KL2 (Chiba Flour Milling Co., Ltd.)
*20 Rheopearl MKL2 (Chiba Flour Milling Co., Ltd.)

TABLE 4

|  |  | Example | | | | |
| --- | --- | --- | --- | --- | --- | --- |
| Component | Component name | 15 | 16 | 17 | 18 | 19 |
|  | Allantoin | 0.5 | 0.5 | 0.5 | 0.5 | 0.5 |
| (F) | N-(hexadecyloxyhydroxypropyl)-N-hydroxyethylhexadecanamide *1 | 8.0 | 8.0 | 8.0 | 8.0 | 8.0 |
| (A) | Isostearyl glyceryl ether *2 | 0.2 | 0.2 |  |  | 0.2 |
|  | Polyoxyethylene/methylpolysiloxane copolymer *3 | 1.5 | 2.5 |  |  |  |
|  | Polyoxyethylene/methylpolysiloxane copolymer *4 |  |  |  |  | 0.75 |
|  | PEG-9 polydimethylsiloxyethyl dimethicone *5 |  |  |  | 2.0 |  |
|  | Polyoxyethylene hydrogenated castor oil *6 |  |  | 4.0 |  |  |
|  | Polyglyceryl diisostearate *7 | 2.0 | 2.0 | 2.0 | 2.0 | 2.0 |
| (D) | Squalane | 8.0 | 20.0 | 8.0 | 8.0 | 8.0 |
|  | Methylpolysiloxane *8 | 8.0 | 8.0 | 8.0 | 8.0 | 8.0 |
|  | Methylpolysiloxane *9 | 4.0 | 4.0 | 4.0 | 4.0 | 4.0 |
|  | Methylpolysiloxane-crosslinked methylpolysiloxane mixture *10 | 5.0 | 5.0 | 5.0 | 5.0 | 5.0 |
| (C) | Di(cholesteryl octyldodecyl) N-lauroyl-L-glutamat *11 | 1.0 | 1.0 | 1.0 | 1.0 | 1.0 |
|  | Di(phytosteryl/2-octyldodecyl) N-lauroyl-L-glutamate *12 | 2.0 | 2.0 | 2.0 | 2.0 | 2.0 |
|  | Dimer dilinoleic acid (phytosteryl/isostearyl/cetyl/stearyl/bchenyl)*11 | 2.5 | 2.5 | 2.5 | 2.5 | 2.5 |
| (B) | Dextrin palmitate *14 | 0.5 | 0.5 | 0.5 | 0.5 | 0.5 |
|  | Magnesium sulfate heptahydrate | 0.7 | 0.7 | 0.7 | 0.7 | 0.7 |
|  | Glycerin (86%) | 10.0 | 10.0 | 10.0 | 10.0 | 10.0 |
|  | 1,3-Butylene glycol | 4.0 | 4.0 | 4.0 | 4.0 | 4.0 |
|  | Eucalyptus extract | 0.33 | 0.33 | 0.33 | 0.33 | 0.33 |
|  | Water-soluble ginger extract (K) | 0.5 | 0.5 | 0.5 | 0.5 | 0.5 |
|  | Hiba arborvitae extract | 2.0 | 2.0 | 2.0 | 2.0 | 2.0 |
|  | Methylparaben | 0.33 | 0.33 | 0.33 | 0.33 | 0.33 |
|  | Succinc acid | 0.1 | 0.1 | 0.1 | 0.1 | 0.1 |

TABLE 4-continued

| Component | Component name | Example 15 | Example 16 | Example 17 | Example 18 | Example 19 |
|---|---|---|---|---|---|---|
| (E) | Sodium hydroxide solution (48%) | 0.07 | 0.07 | 0.07 | 0.07 | 0.07 |
| | Water | 38.77 | 25.77 | 36.47 | 38.47 | 39.52 |
| | Total | 100.0 | 100.0 | 100.0 | 100.0 | 100.0 |
| | Component (A) | 3.7 | 4.7 | 6.0 | 4.0 | 2.95 |
| | Component (B) | 0.5 | 0.5 | 0.5 | 0.5 | 0.5 |
| | Component (C) | 5.5 | 5.5 | 5.5 | 5.5 | 5.5 |
| | Component (D) | 8.0 | 20.0 | 8.0 | 8.0 | 8.0 |
| | Component (E) | 38.77 | 25.77 | 36.47 | 38.47 | 39.52 |
| | Component (F) | 8.0 | 8.0 | 8.0 | 8.0 | 8.0 |
| | Viscosity (Pa · s) | 48 | 43 | 58 | 121 | 85 |
| Evaluation | Water evaporation suppression rate (%) | 49 | 58 | 45 | 42 | 47 |
| | Skin-covering feeling | 5 | 5 | 5 | 4.5 | 5 |
| | Skin-covering feeling | 5 | 5 | 5 | 5 | 5 |
| | No stickiness and no uncomfortable feeling | 5 | 3 | 2.5 | 4.3 | 5 |
| | Storage stability (room temperature, 1 day) | A | A | A | A | A |
| | Storage stability (room temperature, 1 month) | A | B | A | A | B |

*1 Sphingolipid E (Kao Corporation)
*2 GE-IS (U) (HLB 2) (Kao Corporation)
*3 Silicone KF-6015 (PEG-3 dimethicone, HLB 4.5 (Shin-Etsu Chemical Co., Ltd.)
*4 Silicone KF-6017 (PEG-10 dimethicone, HLB (Shin-Etsu Chemical Co., Ltd.)
*5 Silicone KF-6028 (PEG-9 polydimethylsiloxyethyldimethicone, HLB 4 (Shin-Etsu Chemical Co., Ltd.)
*6 EMALEX HC-5K (PEG-5 hydrogenated castor oil, HLB 5 (Nippon Emulsion Co., Ltd.)
*7 Cosmol 42V (polyglyceryl-2 diisostearate, HLB 4) (Nisshin Oilio Group Ltd.)
*8 Silicone KF-96A-2CS (Shin-Etsu Chemical Co., Ltd.)
*9 Silicone KF-96A-6CS (Shin-Etsu Chemical Co., Ltd.)
*10: Silicone KSG-16 (Shin-Etsu Chemical Co., Ltd.)
*11 ELDEW GL-202 (Ajinomoto Co., Inc.)
*12 ELDEW PS-203 (Ajinomoto Co., Inc.)
*13 Plandool-H (Nippon Fine Chemical Co., Ltd.)
*14 Rheopearl KL2 (Chiba Flour Milling Co., Ltd.)

TABLE 5

| Component | Component name | Example 20 | Example 21 | Comparative example 5 | Comparative example 6 |
|---|---|---|---|---|---|
| (F) | N-(hexadecyloxyhydroxypropyl)-N-hydroxyethylhexadecanamide *1 | | 8.0 | | |
| (A) | Polyoxyethylene/methylpolysiloxane copolymer *3 | 1.5 | 1.5 | 1.5 | 1.5 |
| | Polyoxyethylene/methylpolysiloxane copolymer *4 | 0.5 | | 0.5 | 0.5 |
| (D) | Squalane | 8.0 | 8.0 | 8.0 | 8.0 |
| | Methylpolysiloxane *8 | 8.0 | 8.0 | 8.0 | 8.0 |
| | Methylpolysiloxane *9 | 4.0 | 4.0 | 4.0 | 4.0 |
| | Methylpolysiloxane-crosslinked methylpolysiloxane mixture *10 | 5.0 | 5.0 | 5.0 | 5.0 |
| (C) | Dimer dilinoleic acid (phytosteryl/isostearyl/cetyl/stearyl/bchenyl)*13 | 2.5 | 2.5 | | 2.5 |
| (B) | Dextrin palmitate *14 | 4.0 | 0.5 | 4.0 | |
| | Magnesium sulfate heptahydrate | 0.7 | 0.7 | 0.7 | 0.7 |
| | Glycerin (86%) | 10.0 | 10.0 | 10.0 | 10.0 |
| | 1,3-Butylene glycol | 6.0 | 6.0 | 6.0 | 6.0 |
| | Methylparaben | 0.33 | 0.33 | 0.33 | 0.33 |
| | Succinic acid | 0.1 | 0.1 | 0.1 | 0.1 |
| | Sodium hydroxide solution 48% | 0.07 | 0.07 | 0.07 | 0.07 |
| (E) | Water | 49.3 | 45.3 | 51.8 | 53.3 |
| | Total | 100.0 | 100.0 | 100.0 | 100.0 |
| | Component (A) | 2.0 | 1.5 | 2.0 | 2.0 |
| | Component (B) | 4.0 | 0.5 | 4.0 | 0.0 |
| | Component (C) | 2.5 | 2.5 | 0.0 | 2.5 |
| | Component (D) | 8.0 | 8.0 | 8.0 | 8.0 |
| | Component (E) | 49.3 | 45.3 | 51.8 | 53.3 |
| | Component (F) | 0.0 | 8.0 | 0.0 | 0.0 |
| | Viscosity (Pa · s) | 70 | 57 | 78 | 68 |

TABLE 5-continued

|  |  | Example | | Comparative example | |
|---|---|---|---|---|---|
| Component | Component name | 20 | 21 | 5 | 6 |
| Evaluation | Water evaporation suppression rate (%) | 16 | 23 | 12 | 9 |
|  | Skin-covering feeling | 2.5 | 3.0 | 1.8 | 2.8 |
|  | Glossiness of skin | 4.0 | 4.8 | 1.5 | 3.3 |
|  | No stickiness and no uncomfortable feeling | 3.8 | 3.5 | 1.0 | 3.5 |
|  | Storage stability (room temperature, 1 day) | A | A | A | A |
|  | Storage stability (room temperature, 1 month) | A | A | B | C |

*1: Sphingolipid E (Kao Corporation)
*3: Silicone KF-6015 (PEG-3 dimethicone, HLB 4.5 (Shin-Etsu Chemical Co., Ltd.)
*4: Silicone KF-6017 (PEG-10 dimethicone, HLB 5 (Shin-Etsu Chemical Co., Ltd.)
*8: Silicone KF-96A-2CS (Shin-Etsu Chemical Co., Ltd.)
*9: Silicone KF-96A-ECS (Shin-Etsu Chemical Co., Ltd.)
*10: Silicone KSG-16 (manufactured by Shin-Etsu Chemical Co., Ltd.)
*13: Plandool-H (Nippon Fine Chemical Co., Ltd.)
*14: Rheopearl KL2 (Chiba Flour Milling Co., Ltd.)

TABLE 6

|  |  | Example | | |
|---|---|---|---|---|
| Component | Component name | 1 | 22 | 23 |
| (F) | Allantoin | 0.5 | 0.5 | 0.5 |
|  | N-(hexadecyloxyhydroxypropyl)-N-hydroxyethylhexadecanamide *1 | 8.0 | 8.0 |  |
|  | Ceramide-2 |  |  | 8.0 |
| (A) | Isostearyl glyceryl ether *2 | 0.2 | 0.2 | 0.2 |
|  | Polyoxyethylene/methylpolysiloxane copolymer *3 | 1.5 | 1.5 | 1.5 |
|  | Polyglyceryl diisostearate *7 | 2.0 | 2.0 | 2.0 |
| (D) | Squalane | 8.0 |  |  |
|  | Liquid isoparaffin*21 |  | 8.0 | 8.0 |
|  | Methylpolysiloxane *8 | 8.0 | 8.0 | 8.0 |
|  | Methylpolysiloxane *9 | 4.0 | 4.0 | 4.0 |
|  | Methylpolysiloxane-crosslinked methylpolysiloxane mixture *10 | 5.0 | 5.0 | 5.0 |
| (C) | Di(cholesteryl octyldodecyl) N-lauroyl-L-glutamate *11 | 1.0 | 1.0 | 1.0 |
|  | Di(phytosteryl/2-octyldodecyl) N-lauroyl-L-glutamate *12 | 2.0 | 2.0 | 2.0 |
|  | Dimer dilinoleic acid (phytosteryl/isostearyl/cetyl/stearyl/bchenyl)*13 | 2.5 | 2.5 | 2.5 |
| (B) | Dextrin palmitate *14 | 0.5 | 0.5 | 0.5 |
|  | Magnesium sulfate heptahydrate | 0.7 | 0.7 | 0.7 |
|  | Glycerin (86%) | 10.0 | 10.0 | 10.0 |
|  | 1,3-Butylene glycol | 4.0 | 4.0 | 4.0 |
|  | Eucalyptus extract | 0.33 | 0.33 | 0.33 |
|  | Water-soluble ginger extract (K) | 0.5 | 0.5 | 0.5 |
|  | Hiba arborvitae extract | 2.0 | 2.0 | 2.0 |
|  | Methylparaben | 0.33 | 0.33 | 0.33 |
|  | Succinic acid | 0.1 | 0.1 | 0.1 |
|  | Sodium hydroxide Solution (48%) | 0.07 | 0.07 | 0.07 |
| (E) | Water | 38.77 | 38.77 | 38.77 |
|  | Total | 100.0 | 100.0 | 100.0 |
|  | Component (A) | 5.5 | 5.5 | 5.5 |
|  | Component (B) | 3.7 | 3.7 | 37 |
|  | Component (C) | 0.5 | 0.5 | 0.5 |
|  | Component (D) | 8.0 | 8.0 | 8.0 |
|  | Component (E) | 38.77 | 38.77 | 38.77 |
|  | Component (F) | 8.0 | 8.0 | 8.0 |
|  | Viscosity (Pa · s) | 48 | 49 | 93 |
| Evaluation | Water evaporation suppression rate (%) | 49 | 46 | 43 |
|  | Skin-covering feeling | 5.0 | 5.0 | 4.3 |
|  | Glossiness of skin | 5.0 | 4.8 | 3.8 |
|  | No stickiness and no uncomfortable feeling | 5.0 | 5.0 | 4.8 |
|  | Storage stability (room temperature, 1 day) | A | A | A |
|  | Storage stability (room temperature, 1 month) | A | A | A |

*1: Sphingolipid E (Kao Corporation)
*2: GE-IS (U) (HLB 2) (Kao Corporation)
*3: Silicone KF-6015 (PEG-3 dimethicone, HLB 4.5 (Shin-Etsu Chemical Co., Ltd.)
*7: Cosmol 42V (polyglycery-21 diisostearate, HLB 4) (Nisshin Oilio Group Ltd.)
*8: Silicone KF-96A-2CS (Shin-Etsu Chemical Co., Ltd.)
*9: Silicone KF-96A-6CS (Shin-Etsu Chemical Co., Ltd.)
*10: Silicone KSG-16 (Shin-Etsu Chemical Co., Ltd.)
*11: ELDEW GL-202 (Ajinomoto Co., Inc.)
*12: ELDEW PS-203 (Ajinomoto Co., Inc.)
*13: Plandool-H (Nippon Fine Chemical Co., Ltd.)
*14: Rheopearl KL2 (Chiba Flour Milling Co., Ltd.)
*21: PARLEAM EX (NOF Corporation)

The invention claimed is:

1. A water-in-oil emulsion composition comprising the following components (A), (B), (C), (D), (E) and (F):
   (A) from 1% by mass to 15% by mass of a lipophilic surfactant having an HLB of from 2 to 6;
   (B) from 0.15% by mass to 8% by mass of a dextrin fatty acid ester having 8 to 22 carbon atoms in the fatty acid moiety;
   (C) from 1% by mass to 20% by mass of at least one oily component selected from the group consisting of a dimer acid ester and an N-acyl amino acid ester,
   (D) a hydrocarbon oil that is liquid at 25° C.,
   (E) water, and
   (F) from 1% by mass to 30% by mass of a ceramide.

2. The water-in-oil emulsion composition according to claim 1, wherein the content of the component (F) is from 1% by mass to 25% by mass in the water-in-oil emulsion composition.

3. The water-in-oil emulsion composition according to claim 1, wherein the component (A) is a nonionic surfactant having an HLB of from 2 to 6, wherein the nonionic surfactant is at least one selected from the group consisting of a silicone surfactant, a polyoxyethylene hydrogenated castor oil, an alkyl glyceryl ether and a polyglycerol fatty acid ester.

4. The water-in-oil emulsion composition according to claim 1, wherein the component (A) is at least one selected from the group consisting of a polyglycerol fatty acid ester and a polyether modified silicone.

5. The water-in-oil emulsion composition according to claim 1, wherein the water-in-oil composition has a viscosity at 25° C. of 15 Pa·s or more and 5000 Pa·s or less and is in a cream form.

6. The water-in-oil emulsion composition according to claim 1, wherein the component (A) is at least one selected from the group consisting of polyether modified silicones.

7. The water-in-oil emulsion composition according to claim 1, wherein the content of the component (A) is from 1.5% by mass to 12% by mass in the water-in-oil emulsion composition.

8. The water-in-oil emulsion composition according to claim 1, wherein the content of the component (B) is from 0.2% by mass to 6% by mass in the water-in-oil emulsion composition.

9. The water-in-oil emulsion composition according to claim 1, wherein the content of the component (C) is from 1.5% by mass to 18% by mass in the water-in-oil emulsion composition.

10. The water-in-oil emulsion composition according to claim 1, wherein the content of component (F) is from 1.5% by mass to 20% by mass in the water-in-oil emulsion composition.

11. The water-in-oil emulsion composition according to claim 1, wherein the component (F) is a compound of the formula (1):

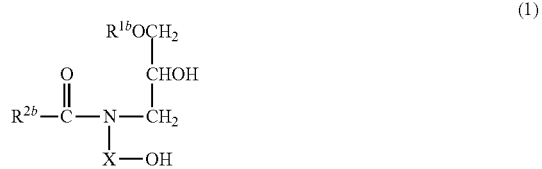

wherein $R^{1b}$ represents a hydrocarbon group having 10 to 26 carbon atoms, $R^{2b}$ represents a hydrocarbon group having 9 to 25 carbon atoms, and X represents —$(CH_2)_n$— wherein n represents an integer of from 2 to 6.

12. The water-in-oil emulsion composition according to claim 1, wherein the component (B) is a dextrin fatty acid ester having 12 to 18 carbon atoms in the fatty acid moiety.

13. The water-in-oil emulsion composition according to claim 1, wherein the component (C) is at least one or more selected from the group consisting of a dimer dilinoleic acid ester and an N-acyl amino acid diester.

14. The water-in-oil emulsion composition according to claim 1, wherein the component (D) is a squalane.

15. The water-in-oil emulsion composition according to claim 1, wherein the water-in-oil has a viscosity at 25° C. of 20 Pa·s or more and 1000 Pa·s or less and is in a cream form.

* * * * *